United States Patent
Redel et al.

(10) Patent No.: US 8,538,508 B2
(45) Date of Patent: Sep. 17, 2013

(54) METHOD AND APPARATUS FOR ECG-SYNCHRONIZED OPTICALLY-BASED IMAGE ACQUISITION AND TRANSFORMATION

(75) Inventors: Thomas Redel, Poxdorf (DE); Estelle Camus, Erlangen (DE); Oliver Meissner, München (DE); Klaus Klingenbeck-Regn, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 2357 days.

(21) Appl. No.: 11/298,779

(22) Filed: Dec. 9, 2005

(65) Prior Publication Data
US 2007/0167833 A1 Jul. 19, 2007

(51) Int. Cl.
*A61B 6/00* (2006.01)
(52) U.S. Cl.
USPC .......................... 600/478; 600/407; 600/476
(58) Field of Classification Search
USPC ................ 600/478, 407, 425, 476; 382/282, 382/284
See application file for complete search history.

(56) References Cited

U.S. PATENT DOCUMENTS

| | | | |
|---|---|---|---|
| 5,830,145 A | | 11/1998 | Tenhoff |
| 6,212,420 B1 * | | 4/2001 | Wang et al. .................... 600/407 |
| 6,842,638 B1 * | | 1/2005 | Suri et al. ...................... 600/425 |
| 2004/0066389 A1 * | | 4/2004 | Skyba et al. ................... 345/619 |
| 2005/0020925 A1 * | | 1/2005 | Kleen et al. .................... 600/476 |
| 2007/0046966 A1 * | | 3/2007 | Mussack et al. .............. 358/1.13 |

FOREIGN PATENT DOCUMENTS
WO WO 97/32182 9/1997

OTHER PUBLICATIONS

"Axial Movement of the Intravascular Ultrasound Probe During the Cardiac Cycle: Implications for Three-Dimensional Reconstruction and Measurements of Coronary Dimensions," Arbab-Zadeh et al., Am. Heart J., vol. 138, No. 5 (1999) pp. 865-873.
Siemens Brochure for Quantcor Software.
Siemens Brochure for Axiom Artis Software.
"True 3-Dimensional Reconstruction of Coronary Arteries in Pateitns by Fusion of Angiography and IVUS (ANGUS) and Its Quantitative Validation," Slager et al., Circulation (2000) pp. 511-516.
"Four-Dimensional Coronary Morphology and Computational Hemodynamics," Wahle et al., Medical Imaging 2001: Image Processing, Sonka et al. Eds., pp. 743-753.
Intravascular Ultrasound: Novel Pathophysiological Insights and Current Clinical Applications, Nissen et al., Circulation (2001), pp. 604-616.

* cited by examiner

*Primary Examiner* — James Kish
*Assistant Examiner* — Christopher Cook
(74) *Attorney, Agent, or Firm* — Schiff Hardin LLP

(57) ABSTRACT

In a method and apparatus for optically-based acquisition of slice images from a vessel of a subject, and for combining the slice images to provide an intuitively recognizable visualization of a pathology in the vessel, slice images of the vessel are acquired during pullback of an optical probe of the optically-based slice imaging system, while simultaneously acquiring an ECG signal from the subject. The slice images and the ECG signal are registered, and slice images acquired at a selected cardiac phase are combined into a scene. The slice images in the scene are subjected to a first data transformation to shift the vessel midpoint in each slice image to the image center of each slice image. After the first data transformation, the slice images in the scene are subjected to a second data transformation to produce the visualization. The second transformation, for example, can be a curved planar reformation to allow the vessel to be shown in longitudinal section.

17 Claims, 4 Drawing Sheets

Image n

Image m

Image o

Image n'

Image m'

Image o'

METHOD AND APPARATUS FOR ECG-SYNCHRONIZED OPTICALLY-BASED IMAGE ACQUISITION AND TRANSFORMATION

BACKGROUND OF THE INVENTION

1. Field of the Invention

The present invention is directed to an OCT (optical coherence tomography) method and apparatus, and in particular to such a method and apparatus for obtaining a sequence of OCT images and for subsequently combining those images into a diagnostic image.

2. Description of the Prior Art

Optical coherence tomography (OCT) is an invasive imaging modality that is currently used for visual assessment of lesions or pathologies in blood vessels, such as stenoses and problematic plaque deposits. To improve such assessment, it is desirable to produce a diagnostic image wherein the portion of the vessel in question is displayed so that the pathology can be intuitively recognized without additional technical outlay, and without additional radiation exposure to the patient.

Arteriosclerotic pathologies of the coronary vessels are the primary cause of death in industrialized nations. Narrowing of the coronary vessels (stenoses) or lipid-filled plaque deposits are the most frequent cause of heart attacks. Prevalent therapy measures are balloon dilation and/or the implantation of stents. A significant pre-condition for the therapy selection and the therapy success is a precise characterization of the pathological situation (lesion).

In addition to determining the length (extent in the vessel) of the lesion, the degree of constriction of the vessel, the diameter of the original, healthy vessel and the wall structure of the vessel are the types of information which contribute toward such a precise characterization of the lesion. It is desirable to know such information not only in the region of the lesion itself, but also at a region or regions downstream from the lesion in terms of blood flow, and a region or region upstream from the lesion in terms of blood flow.

OCT is a known imaging modality that allows images to be obtained from the inside of a vessel using an intravascular imaging catheter. A general description of OCT is available, for example, from PCT Application WO 97/32182. OCT systems operate in a light wavelength range of approximately 1300 nm (near-infrared range). Light in this wavelength range is emitted from a lens of the catheter into the vessel wall, and the reflection of the emitted light from the vessel wall is detected with depth resolution by interferometry. Image information is obtained from various adjacent points of the vessel wall by rotation of the radiated light beam, and this image information is combined into a 2D image representing a "slice" of the vessel in the plane of the radiated light beam. Additionally, the catheter can be moved along the longitudinal direction of the vessel during image acquisition, in order to obtain successive images of the vessel. The OCT catheter is inserted into the vessel up to a selected point, and is then withdrawn in a continuous, monitored movement, known as a "pullback," during which images are successively obtained, so that a "stack" of two-dimensional slice images is acquired. These images can be combined offline (i.e., after acquisition) to form a three-dimensional dataset. In general, however, only the current two-dimensional slice image is actually visible on the display screen that is used during the image acquisition. These individual OCT images have a very high spatial resolution. Dependent on the distance of the vessel wall from the catheter, the resolution is below approximately 40 µm in the x, y direction (slice plane) and is in the range between 40 to 100 µm in the z-direction (pullback direction), depending on the frame rate and withdrawal speed. For example, the light beam can be rotated in the slice plane at a rotational frequency of up to 30 Hz.

For characterization of a stenosis in the catheter laboratory (cathlab) a series of techniques are currently available, but each has certain inadequacies associated therewith.

The most important conventional method for characterization of a lesion is angiography. Angiography equipment available today provided information only about the vessel itself, but does not supply information regarding the morphology (appearance and extent) of the lesion. Nevertheless, angiography results can be used for further therapy selection. In addition to the initial assessment of vessel constrictions that can be seen in the angiography image, automated evaluation programs can be used for quantitative coronary angiography (QCA). An example is the Quantcor software available from Siemens AG. Such programs typically provide information about the length of a stenosis, the reference diameter (vessel diameter before and after the lesion, minimum/average/maximum vessel diameter, and maximum diameter reduction in the constriction).

The lack of information regarding the vessel structure in the region of the lesion, and the two-dimensional nature of angiography exposures are limiting factors in assessing a therapy using this technique. Errors primarily occur in the length measurement, due to the lesion not lying precisely in the plane of the angiography image, and thus appearing foreshortened in the angiography image. This type of problem, however, can be addressed by the use of three-dimensional reconstructions from two x-ray projections using software also available from Siemens AG known as AXIOM ARTIS with Interventional Cardiac 3D (IC3D). This requires, however, that the patient receive two x-ray doses. Intravascular imaging using IVUS (intravascular ultrasound) can provide additional information regarding the structure of the vessel wall. Background concerning intravascular ultrasound can be found in "Intravascular Ultrasound: Novel Pathophysiological Insights and Current Clinical Applications," Nissen et al., Circulation (2001) pages 604-616. All significant, therapy-determining quantities of the lesion can be determined with this two-dimensional slice imaging technique. IVUS therefore has become the most prevalent technique for characterization of stenoses and plaque deposits. Like OCT, IVUS involves the withdrawal (pullback) of a probe, in this case an ultrasound probe, through a vessel. Despite the aforementioned advantages of IVUS, the evaluation of IVUS pullback sequences is subject to limitations.

Due to movement of the heart through successive cardiac cycles, a shifting of the catheter in the vessel ensues in the imaging plane, as well as periodically along the vessel axis (longitudinal direction). This problem is described in "Axial Movement of the intravascular Ultrasound Probe During the Cardiac Cycle: Implications for Three-Dimensional Reconstruction and Measurements of Coronary Dimensions," Arbab-Zadeh et al., Am. Heart J., Vol. 138, No. 5 (1999), pages 865-873. Analyzing the image sequence while taking these factors into account requires experience on the part of the interpreting physician, particularly when comparing various vessel sections (longitudinal scans). Automatic quantifications of IVUS images would require an automatic segmentation of the IVUS images, which currently can be achieved only to a limited extent due to the limited resolution, the fluctuating intensities and contrasts, and by artifacts in the IVUS images.

An improved approach is known as ANGUS, and is described in the article "True 3-Dimensional Reconstruction of Coronary Arteries in Patients by Fusion of Angiography and IVUS (ANGUS) and Its Quantitative Validation," Slager et al., Circulation (2000) pages 511-516. In this technique, pullback of the IVUS catheter is registered with a biplanar x-ray system from two projection directions. The three-dimensional course of the vessel then can be reconstructed from this information, and with ECG triggering of the images. Such a biplanar x-ray system, however, is available only in a limited number of catheter laboratories, and also requires an additional radiation exposure for the patient.

An alternative to x-ray imaging with ECG triggering is the use of a positioning system, wherein a sensor is mounted at the tip of the imaging sensor, the sensor providing an indication of the position and orientation of the imaging probe to an extracorporeal positioning system. Such a technique is described in U.S. Pat. No. 5,830,145. The use of the additional extracorporeal positioning system and special catheters, however, are necessary to implement this technique.

A method is described in "Four-Dimensional Coronary Morphology and Computational Hemodynamics," Wahle et al., "Medical Imaging 2001: Image Processing" Sonka et al. eds. (pages 743-753) wherein the ECG is recorded in parallel with the IVUS (ANGUS) pullback, and thus a cardiac phase, determined or selected from the ECG can be associated with the individual IVUS images. A 4D model of the vessel section, used to simulate blood flow in the vessel, can be determined from this information.

It is also possible to visualize the consistency (composition, formation) of the vessel wall using OCT. The determination of all significant quantities is additionally possible for characterization of a lesion. An advantage of OCT is the high resolution of approximately 40 μm, a good high-contrast representation of the vessel sections, and the absence of shadowing effects due to calcifications.

SUMMARY OF THE INVENTION

It is an object of the present invention to provide an optically-based slice imaging apparatus and method (such as an OCT or OFDI method and apparatus) that allow a meaningful image of a pathological vessel segment to be obtained without a positioning system and without additional radiation exposure to the patient, wherein the pathological vessel segment is seen in an intuitively recognizable manner, with a resolution that is sufficient for a therapy selection.

It is a further object of the present invention to provide such a method and apparatus that allow the image of the pathological vessel to be shown time-dependent and/or in a quasi-3D manner.

The above object is achieved in accordance with the present invention in an optically-based slice imaging method and apparatus wherein acquisition of slice images of a pathology-containing vessel are acquired during pullback of the optical probe, with simultaneous acquisition of an ECG signal from the subject. The slice images and the ECG are registered, so that the respective points in time at which the slice images were individually acquired are associated with respective points in time along the ECG signal. The slice images are then re-sorted so that slice images belonging to a pre-selected cardiac phase (i.e., a recurring point in time in each successive cardiac cycle) are combined into a scene. A centering catheter preferably is used so that the slice images will be oriented perpendicularly to a center axis of the vessel, but because the vessel itself is not precisely linear and the pullback of the probe through the vessel will not necessarily be precisely centered within the vessel, the center of the vessel in the respective slice images will not coincide from image-to-image. Therefore, a data transformation is undertaken with regard to each slice image in the scene, to shift the vessel midpoint to the image center in each slice image in the scene. The thus-transformed images in the scene are then subjected to a further transformation to display the scene in longitudinal section. This last transformation corresponds to the known "curved planar reformation" (CPR) in CT angiography.

The user can select the cardiac phase and/or the angle of the longitudinal section for visualization in the longitudinal section image. The longitudinal section image can then be easily used to manually or automatically determine the aforementioned characteristics that are necessary for therapy selection.

DESCRIPTION OF THE PREFERRED EMBODIMENTS

Figure 1:
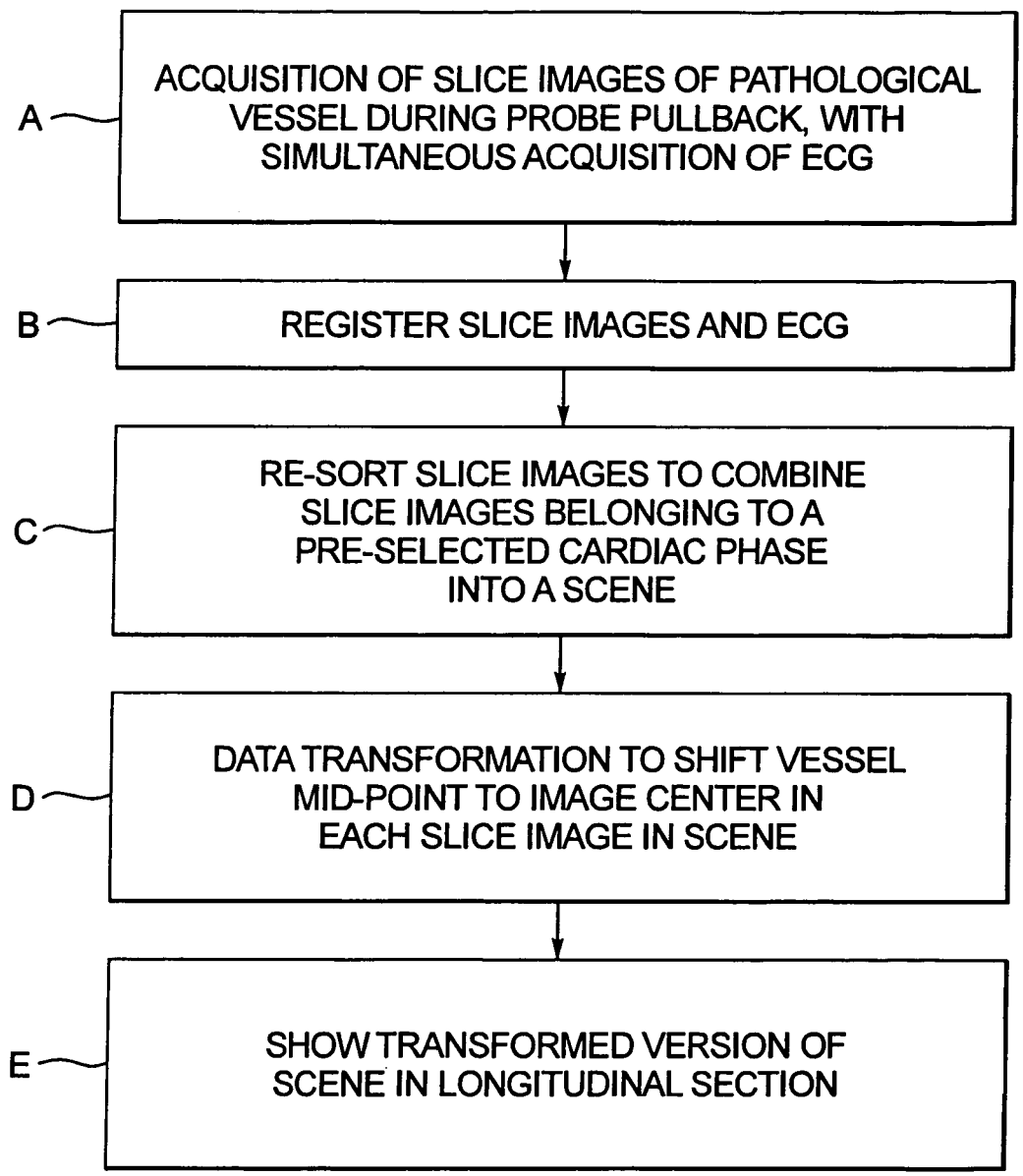
FIG. 1 is a flowchart of a method for optically-based slice image acquisition and combination in accordance with the invention.

The basic steps of an optically-based slice imaging method, for acquisition of the slice images as well as combining the slice images into a diagnostic image, according to the invention are shown in FIG. 1.

In step A, a series of slice images of a pathology-containing vessel are acquired during pullback of an optical probe, such as an OCT probe or an OFDI probe. The optical probe can be positioned in the vessel at a location downstream from the suspected location of a lesion (pathology) so that during pullback a succession (series) of slice images are acquired not only from the lesion-containing portion of the vessel, but also from portions downstream and upstream therefrom. As also indicated in step A, an ECG signal is acquired from the subject during pullback of the optical probe. Preferably a centering catheter is used so that the slice images will all be oriented perpendicularly to the center axis of the vessel. Alternatively, known external position and orientation sensors can be used with a navigation system.

In step B, the slice images obtained during pullback of the optical probe are registered with the ECG signal, meaning that the point in time of the acquisition of each slice image is correlated with a point in time along the ECG signal.

The ECG signal is a periodic signal representing successive cardiac cycles. Each point in the ECG signal represents a point in time in each cardiac cycle. Each point in time of the ECG signal, therefore, represents a particular phase of a heartbeat. In step C, the physician selects a particular cardiac phase. This cardiac phase thus has the same point in time associated therewith in each repetition of the cardiac cycle in the ECG signal. In step C, the slice images a re-sorted, so that slice images belonging to the selected cardiac phase are combined into a scene. Thus one slice image from each cardiac cycle, occurring at the same point in time in the respective cardiac cycles, will be identified and these identified slice images will be combined into the scene.

The vessel, of course, is not itself precisely linear, and the optical probe will not necessarily be situated precisely in the center of the vessel. Therefore, the respective vessel midpoints in the slice images will not coincide with the image center from slice image-to-slice image. Therefore, in step D an electronic data transformation of the data representing each slice image in the scene is undertaken to shift the vessel midpoint in each slice image to the image center. The result of step D is that the vessel midpoint is at the same location in each slice image in the scene.

In step E, the slice images in the scene that were transformed in step D are subjected to a further transformation to show the scene in longitudinal section. The further transformation that takes place in step E corresponds to the technique known as "curved planar reformation" (CPR) from CT angiography. The physician can select the heart phase or the angle of the longitudinal section that will be displayed, and from the displayed image can determine appropriate quantities, such as stenosis length, the reference diameter, etc. by interactive determination of measurement points. Alternatively, the longitudinal section is in a form that is suitable for many types of known automatic analysis software programs.

In step C, the selection of the cardiac phase can be made in any suitable manner, such as by touching or designating a point in a display of the ECG signal (for example the R-wave), or by designating a percentage of each cardiac cycle according to a time duration. Moreover, the selection in step C can be a pre-selection, made before the acquisition of the slice images in step A. If such a pre-selection is made, the acquisitions of the slice images themselves are triggered by the pre-selection criterion, so that a slice image is acquired, for example, only upon the occurrence of each successive R-wave. The "sorting" of the slice images thus takes place simultaneously with the acquisition thereof.

Figure 3:
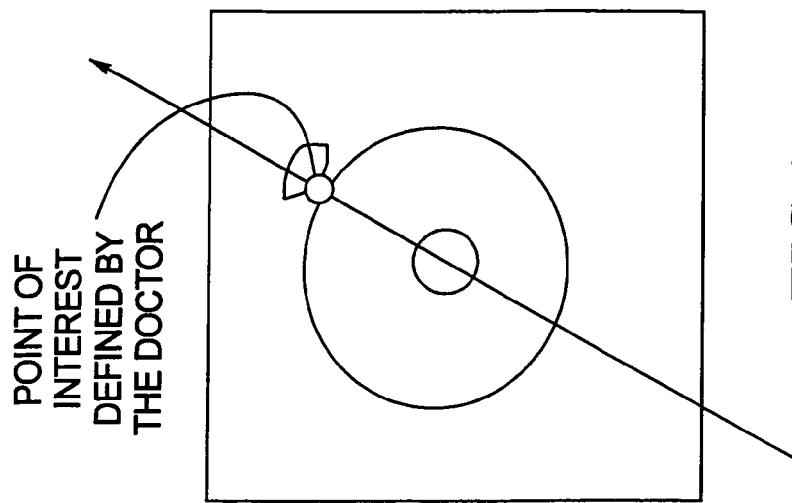
FIG. 3 schematically illustrates an example of a point of interest defined by the physician.
Figure 2:
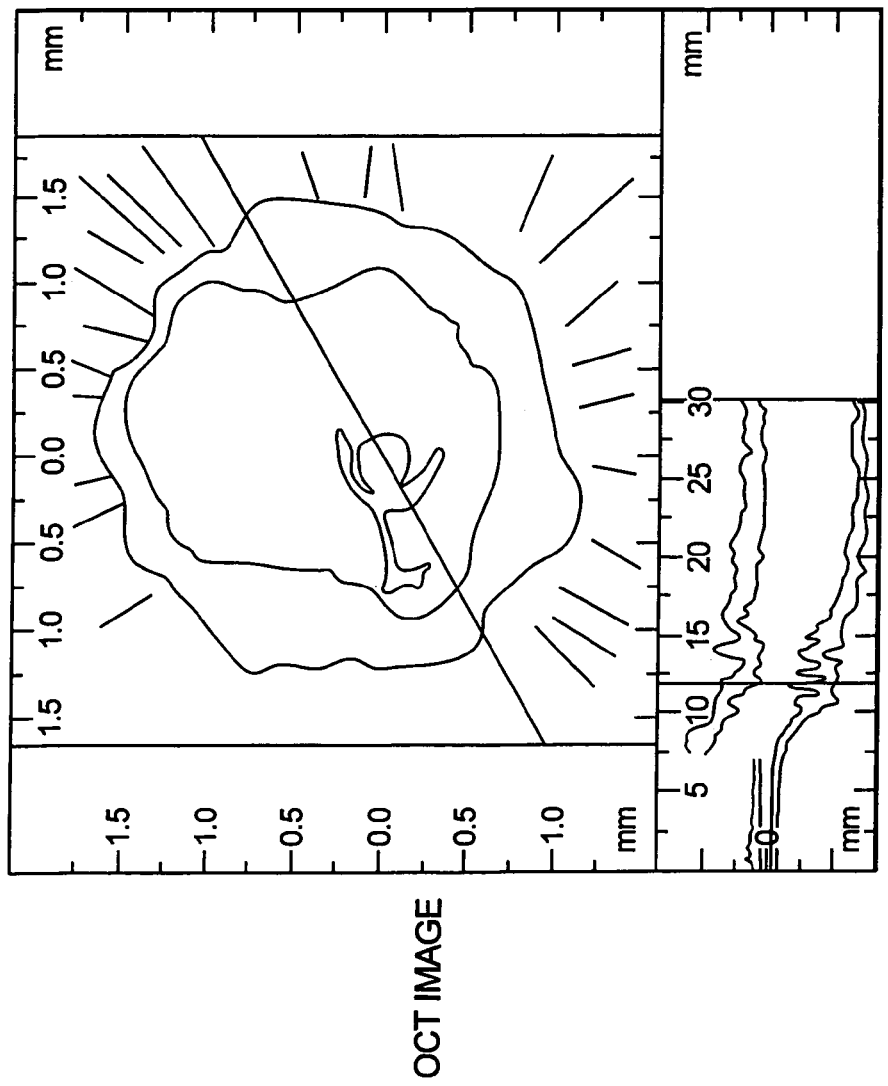
FIG. 2 schematically illustrates a display viewed by physician to allow the physician to select a point of interest for use in sorting the slice images for combining those slice images.
Figure 4A:
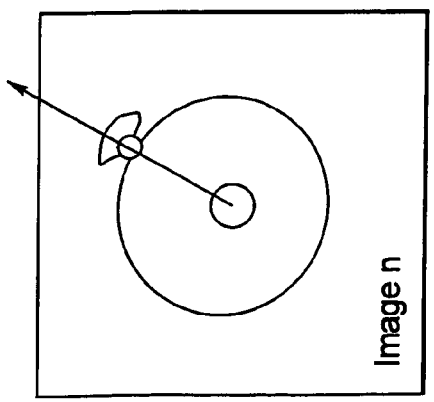
FIGS. 4a, 4b and 4c schematically illustrate, in a manner corresponding to the schematic illustration of FIG. 3, the shifting position of the point of interest in respective slice images before a transformation of the slice images.
Figure 4B:
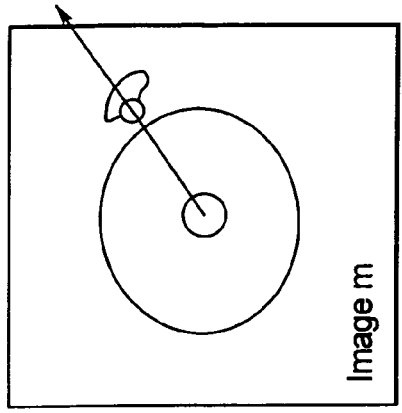
Figure 4C:
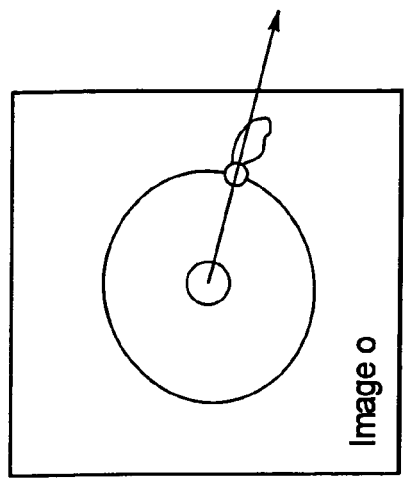

In an alternative embodiment, the last-transformed version of the scene need not be shown in longitudinal section, as specified in step E of the exemplary embodiment of FIG. 1, but can be additionally, or alternatively, shown in a multi-curved reformation version. For this purpose, in a display of one of the slice images, as schematically illustrated in FIG. 2, the physician selects a point of interest in the image, such as by designating a line through the slice image, as shown in FIG. 2. The actual image shown in FIG. 2 is then electronically converted or transformed into a best-fit circular image as shown in FIG. 3, with the point of interest defined by the doctor being represented as the angle coordinate in a polar coordinate representation of the point. This same representation of the defined point is then made automatically electronically for all images in the scene. If the designation is made by the physician in image n, for example, in the scene, as indicated in FIG. 4a, the same schematic designation will be made in preceding images in the scene (represented by image m in FIG. 4b), as well as succeeding images in the scene, (represented by image o in FIG. 4c).

Figure 5A:
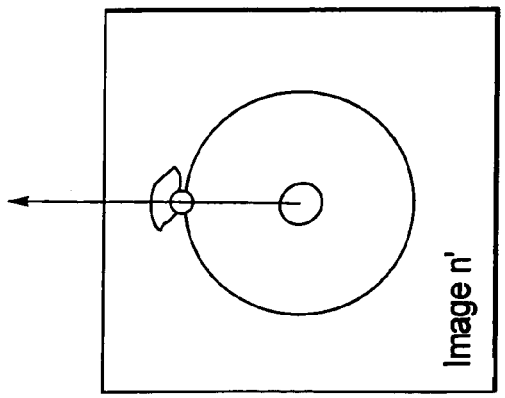
FIGS. 5a, 5b and 5c respectively illustrate slice images 4a, 4b and 4c after a transformation dependent on the point of interest selected by the physician.
Figure 5B:
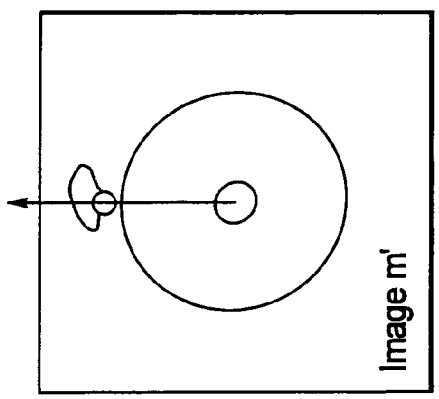
Figure 5C:
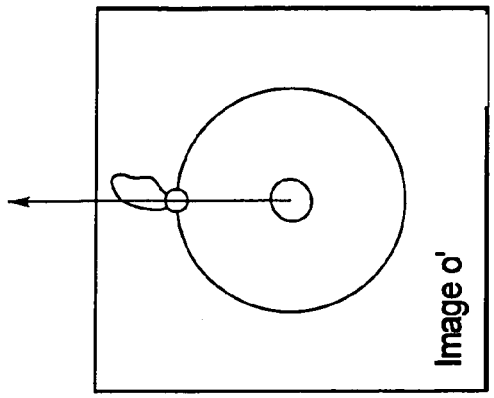

An automatic electronic transformation is then undertaken, wherein all of the images are rotated so that the selected angular cords are transferred to be shown at a defined angle (for example 0°). The rotation angles are interpolated in intermediate images. For each image of the scene, a rotation angle is determined so that a straight path results for the line that actually proceeds in a twisted manner through all of the points along the vessel. This results in a scene wherein all of the individual images have the same angular coordinates, as indicated in FIGS. 5a, 5b and 5c after rotation, respectively corresponding to FIGS. 4a, 4b and 4c before transformation.

Figure 6:
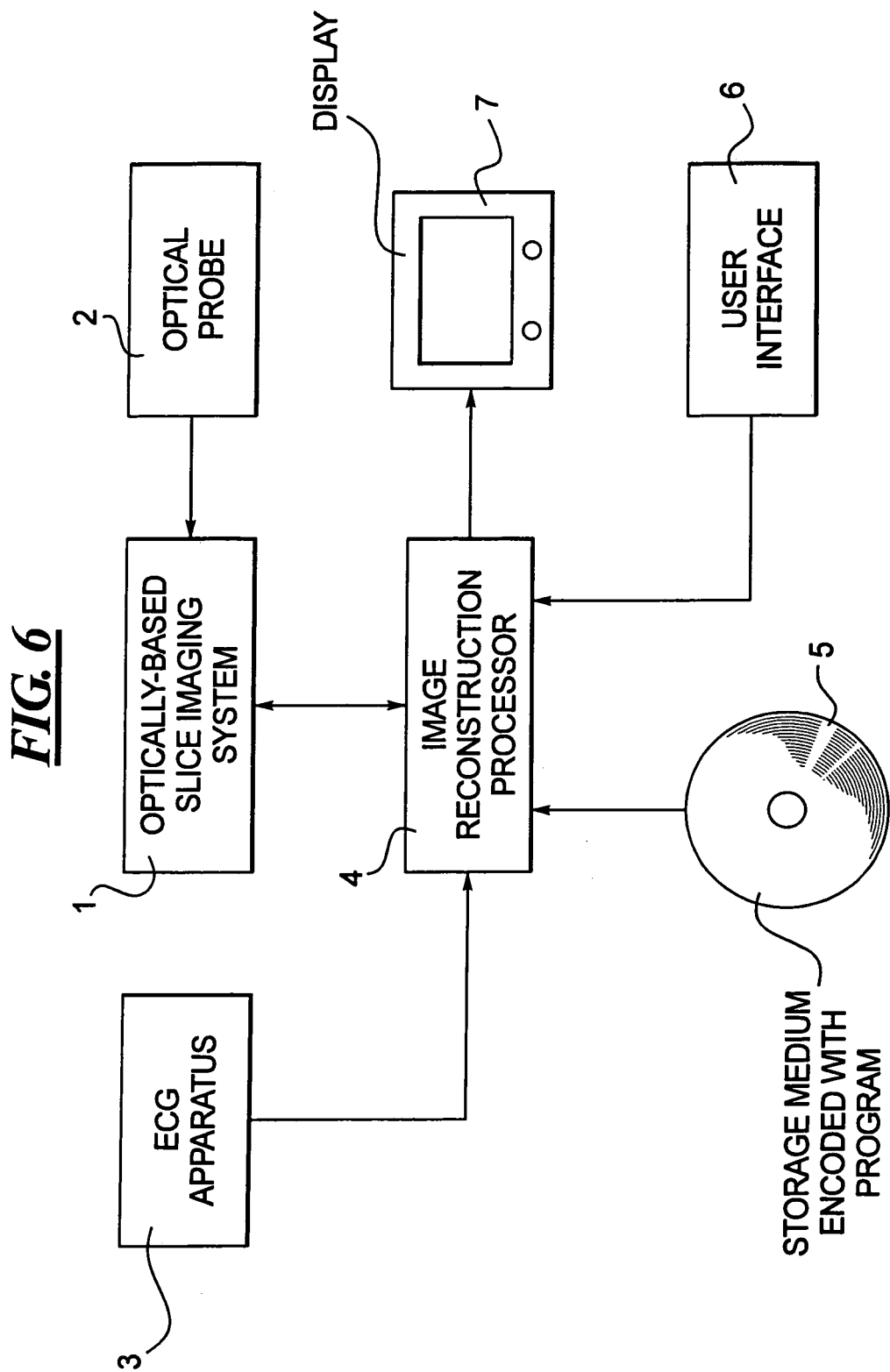
FIG. 6 is a block diagram illustrating the basic components of an apparatus constructed and operating in accordance with the present invention, wherein the image reconstruction processor is loaded with a storage medium encoded with a computer program in accordance with the present invention.

A schematic illustration of the basic components of an apparatus for performing the above-described embodiments of the method is shown in FIG. 6. The apparatus includes an optically-based slice imaging system, such as an OCT system or an OFDI system. The optically-based slice imaging system 1 includes an optical probe 2 that is adapted to be inserted in a known manner in a pathology-containing vessel of a patient (not shown). An ECG apparatus 3 is also provided to obtain an ECG signal in a known manner from the same patient during pullback of the optical probe 2. Images acquired by the optically-based slice imaging system 1 are supplied, together with the ECG signal from the ECG apparatus 3, to an image reconstruction processor 4 connected to those components. The image reconstruction processor 4 is loaded with a storage medium 5 that is encoded, in computer-readable form, with a program for operating the image reconstruction processor 4 to execute one or more embodiments of the inventive method, as described above. During the implementation of the method, a physician makes appropriate entries into the image reconstruction processor 4 to make the aforementioned selections. Necessary information for aiding the physician in making these selections is displayed on a display 7, connected to the image reconstruction processor 4, during the implementation of the method. The final image produced as a result of the method is also displayed at the display 7.

The connection between the image reconstruction processor 4 and the optically-based slice imaging system 1 is shown as being bi-directional, to allow the physician to make the aforementioned pre-selection of the cardiac phase at which the optically based slice imaging system will acquire the individual slice images. For this purpose, the optically-based slice imaging system 1 can receive the ECG signal from the ECG apparatus via the image reconstruction processor 4, or alternatively a direct connection can be provided between the ECG apparatus and the optically-based slice imaging system 1. Of course, it is also possible for the optically-based slice imaging system 1 itself to have its own user interface, through which the aforementioned pre-selection can be made by the physician.

The inventive method, apparatus and encoded storage medium allow parameters that are important for selecting a therapy to relieve a vessel occlusion to be made simply and semi-automatically from slice images obtained using an optically-based slice imaging system, without the use of additional devices and without exposing the subject to an x-ray dose. The method and apparatus take advantage of the high-resolution that is achievable with optically-based slice imaging, and allow quantitative 4D evaluation to be made for diagnostic purposes. The vessel scene can be displayed in a manner that allows intuitive visualization of the occlusion. It is also possible to superimpose the image achieved in accordance with the present method and apparatus with another image, such as a CT image, or another image obtained during a different examination of the same subject, so that the progress of therapy can be monitored or to allow comparison of the occluded vessel with an image of the vessel when in a non-pathological state.

Although modifications and changes may be suggested by those skilled in the art, it is the intention of the inventors to embody within the patent warranted hereon all changes and

We claim as our invention:

1. A method for acquiring a plurality of slice images of a vessel, comprising the steps of:
in an optical coherence tomography procedure, executing a pullback of an optical probe through a vessel of a subject while successively acquiring a plurality of optically-based cross-sectional slice images of the vessel with said optical probe;
combining slice images, from among said plurality of slice images, into a 2D scene showing a longitudinal section of the vessel, each slice image in said 2D scene being comprised of data and each having an image center;
subjecting each slice image in said 2D scene to a first data transformation to shift a midpoint of the vessel in each slice image in the 2D scene to coincide with the image center of each slice image;
after said first data transformation, subjecting each slice image in the 2D scene to a second data transformation to obtain a twice-transformed 2D image of said longitudinal section vessel in a visually displayable form; and
displaying said twice-transformed 2D images to form a display of said 2D scene in which the image center of each displayed twice-transformed image coincides with said midpoint of said vessel.

2. A method as claimed in claim 1 wherein the step of subjecting said slice images to a second transformation comprises subjecting said slice images to a curved planar reformation to display said vessel in said longitudinal section.

3. A method as claimed in claim 1 wherein the step of subjecting said slice images to a second data transformation comprises:
in one of said slice images in said 2D scene, designating a point of interest;
representing said point of interest in said one of said slice images as an angle coordinate in a polar coordinate system representation of said one of said slice images;
automatically electronically identifying an angle coordinate in said polar coordinate system of said point of interest in all other slice images in said 2D scene; and
displaying each of the slice images in said scene in respective polar coordinate system representations with the angle coordinate of the point of interest in each slice image at a same angle in all of said representations.

4. A method as claimed in claim 3 wherein the step of designating a point of interest comprises allowing manual designation of said point of interest in said one of said slice images in said scene.

5. A method as claimed in claim 1 comprising executing said pullback of said optical probe through said vessel of said subject while simultaneously acquiring an ECG signal of the subject, and registering said plurality of slice images with said ECG signal, and combining slice images, from among said plurality of slice images, acquired at a selected cardiac phase represented by said ECG signal, into said 2D scene.

6. A method as claimed in claim 5 wherein the step of registering said slice images and said ECG signal comprises, after acquiring said slice images, correlating a point in time at which each of the slice images was acquired with a respective point in time in the ECG signal.

7. A method as claimed in claim 5 wherein the step of registering said slice images and said ECG signal comprises pre-selecting a point in time in a cardiac cycle of the subject in said ECG signal, and acquiring said slice images only at respective points in time coinciding with the selected point in time in the ECG signal.

8. A method as claimed in claim 5 wherein said ECG signal represents a cardiac cycle waveform, and comprising selecting said cardiac phase by designating a characteristic in said waveform that recurs in said ECG signal from cycle-to-cycle.

9. A method as claimed in claim 5 wherein said ECG signal represents a plurality of cardiac cycles each having a substantially equal time duration, and comprising selecting said cardiac phase by designating a percentage of said time duration.

10. A method as claimed in claim 1 comprising acquiring said optically-based slice images by a cross-sectional imaging technique selected from the group consisting of optical coherence tomography and optical frequency domain imaging.

11. A method as claimed in claim 1 comprising executing said pullback of said probe using a centering catheter that carries said probe.

12. An apparatus for acquiring a plurality of slice images of a vessel, comprising:
an optically-based cross-sectional slice imaging system having an optical probe adapted for insertion in a vessel of the subject to allow a pullback of an optical probe through a vessel of a subject while successively acquiring a plurality of optically-based slice images of the vessel with said optical probe;
a computer configured to combine slice images, from among said plurality of slice images, into a 2D scene showing a longitudinal section of the vessel, each slice image in said 2D scene being comprised of data and each having an image center, and configured to subject each slice image in said 2D scene to a first data transformation to shift a midpoint of the vessel in each slice image in the 2D scene to coincide with the image center of each slice image, and each slice image in the 2D scene, after said first data transformation, to a second data transformation to obtain a twice-transformed image of said vessel in a visually displayable form;
a display in communication with said computer; and
said computer being configured to displaying said twice-transformed 2D images to form a display of said 2D scene in which the image center of each displayed twice-transformed image coincides with said midpoint of said vessel.

13. An apparatus as claimed in claim 12 wherein said optically-based cross-sectional slice imaging system is an imaging system selected from the group consisting of optical coherence tomography systems and optical frequency domain imaging systems.

14. An apparatus as claimed in claim 12 wherein said optical probe comprises a centering catheter.

15. An apparatus as claimed in claim 12 comprising an ECG system adapted to interact with the subject to obtain an ECG signal from the subject, and wherein said optically-based slice imaging system is configured to acquire said plurality of optically-based slice images of the vessel simultaneously with acquisition of said ECG signal by said ECG system, and wherein said computer is configured to register said plurality of optically-based sliced images of the vessel with said ECG signal and to combine slice images, from among said plurality of slices images, acquired at a selected cardiac phase represented by said ECG signal, into said 2D scene.

16. A non-transitory computer-readable storage medium encoded with a program, loadable into a processor of a computerized system that includes an optically-based cross-sectional slice imaging system with an optical probe to acquire slice images from a subject allowing a physician to execute a pullback of an optical probe through a vessel of a subject while successively acquiring a plurality of optically-based slice images of the vessel with said optical probe; said program causing said processor to:
- combine slice images, from among said plurality of slice images, into a 2D scene showing a longitudinal section of the vessel, each slice image in said scene being comprised of data and each having an image center;
- subject each slice image in said 2D scene to a first data transformation to shift a midpoint of the vessel in each slice image in the 2D scene to coincide with the image center of each slice image;
- after said first data transformation, subject each slice image in the 2D scene to a second data transformation to obtain an image dataset of said vessel in a visually displayable form; and
- to display at a monitor displaying said twice-transformed 2D images to form a display of said 2D scene in which the image center of each displayed twice-transformed image coincides with said midpoint of said vessel.

17. A storage medium as claimed in claim 16 wherein said computerized system comprises an ECG acquisition system that acquires an ECG signal from the subject simultaneously with the acquisition of said plurality of optically-based images, and wherein said program further causes said processor to register said optically-based slice images with said ECG signal and to combine slice images, from among said plurality of slice images, acquired at a selected cardiac phase represented by said ECG signal, into said 2D scene.

* * * * *